US005676960A

United States Patent [19]
Myles

[11] Patent Number: 5,676,960
[45] Date of Patent: Oct. 14, 1997

[54] COMPOSITION FOR TREATING INSECTS

[76] Inventor: Timothy G. Myles, Faculty of Forestry University of Toronto 33 Willlocks Street, Toronto, Ontario, Canada, M5S 3B3

[21] Appl. No.: 624,345

[22] Filed: Apr. 3, 1996

Related U.S. Application Data

[62] Division of Ser. No. 414,141, Mar. 30, 1995, Pat. No. 5,609,879, which is a continuation of Ser. No. 22,043, Feb. 24, 1993, abandoned.

[51] Int. Cl.$^6$ .................................................. A01N 25/24
[52] U.S. Cl. .................................................. 424/410; 424/84
[58] Field of Search ............................. 424/410, 84

[56] References Cited

U.S. PATENT DOCUMENTS

| 4,282,207 | 8/1981 | Young et al. ............................ 424/486 |
| 4,352,833 | 10/1982 | Young et al. ............................ 427/4 |
| 5,230,894 | 7/1993 | Robert et al. ............................ 424/411 |

OTHER PUBLICATIONS

Su, N.Y. and Scheffrahn, R.H., "Laboratory Evaluation of Two Slow-acting Toxicants Against Formosan and Eastern Subterranean Termites (Isoptera: Rhinotermitidae)", J. of Econ. Entomol., vol. 84, No. 1, issued Feb. 1991, pp. 170–175.

Myles, T.G. and Grace, J.K., "Behavioral Ecology of the Eastern Subterranean Termite in Ontario as a Basis for Control", pp. 547–554, In: Proceedings of the Ontario Ministry of the Environmental Technology Transfer Conference, vol. 11, pp. 547–554 (Held on Nov. 25–26, 1991 in Toronto, Ontario Canada).

*Primary Examiner*—Melvyn I. Marquis
*Assistant Examiner*—Robert H. Harrison
*Attorney, Agent, or Firm*—I. Robert Silverman; Robert L. Andersen

[57] ABSTRACT

A method of treating a population of social insects includes applying topically to the insect a composition comprising a carrier and an active ingredient. The composition provides a coating that adheres to the insect and is groomable and ingestible by other insects to distribute the active ingredient within the population. In accordance with a preferred embodiment, the composition includes sulfluramid as an active ingredient and an air dryable resin as a carrier. A trap for collection of insects controls temperature within the trap to promote recruitment and also drive the insects to a collection area where they may be treated.

5 Claims, 5 Drawing Sheets

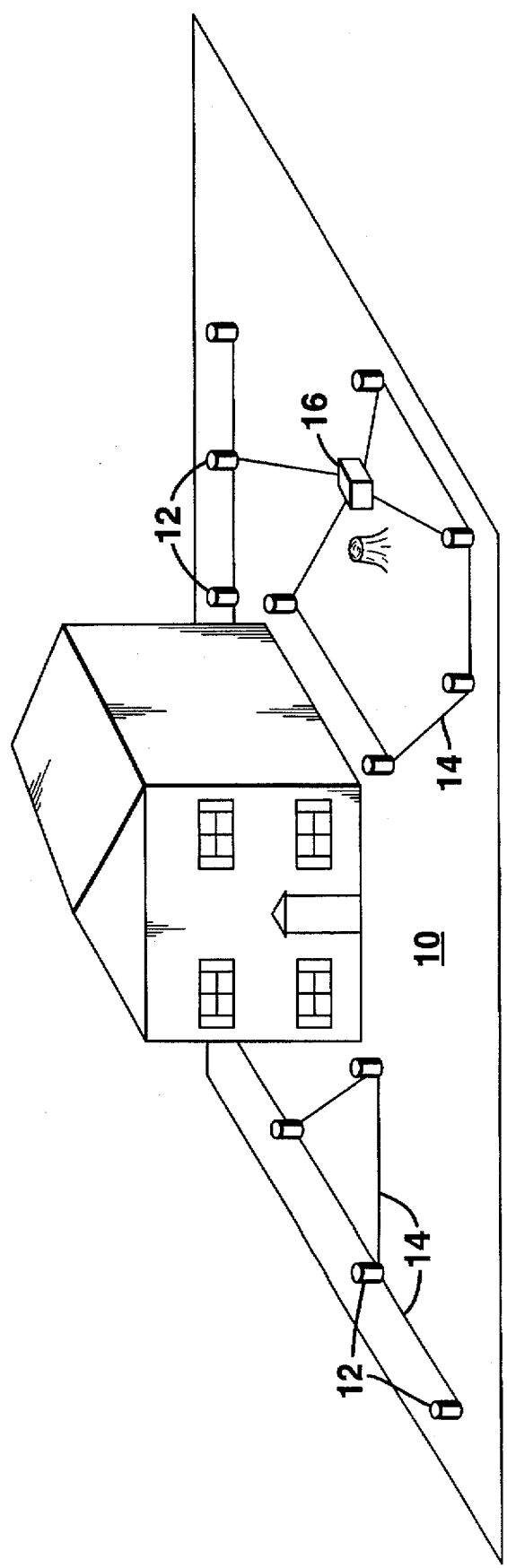

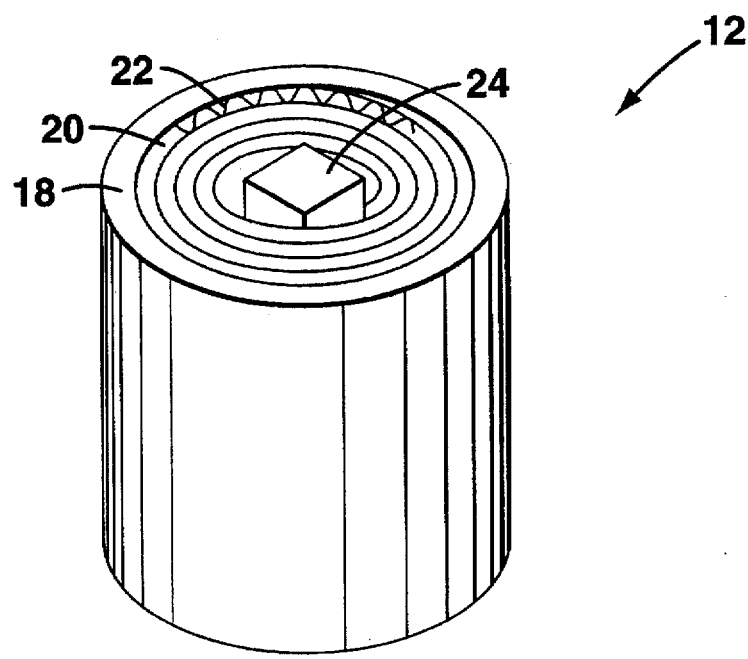
FIG_2
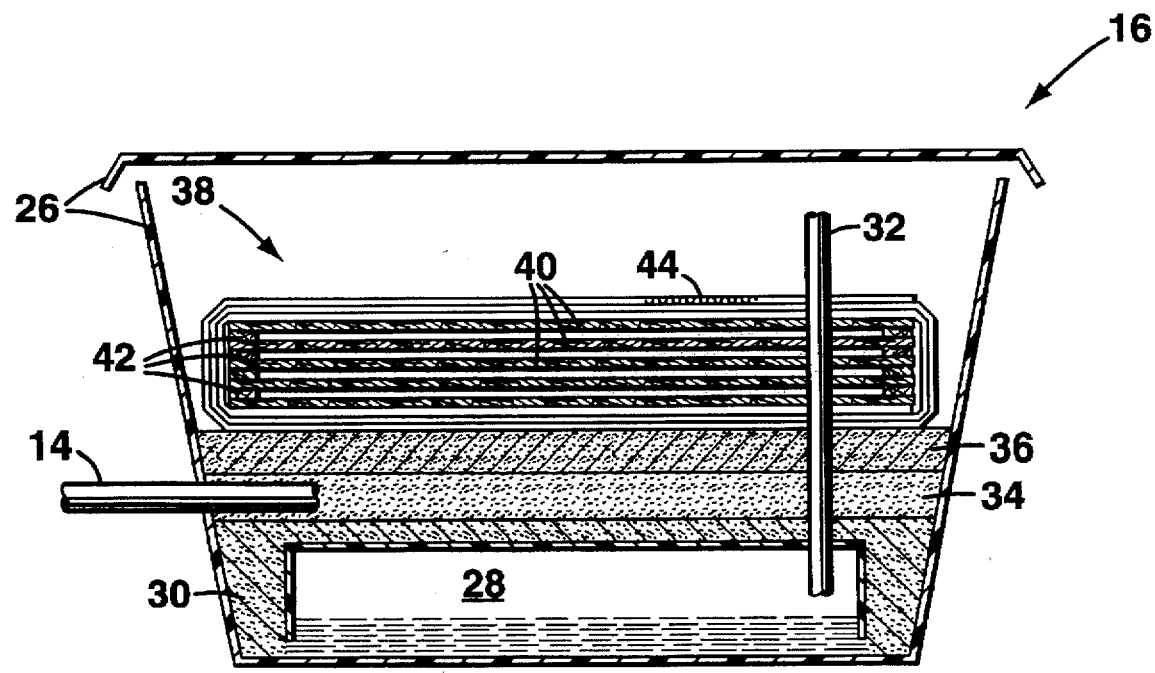
FIG_3

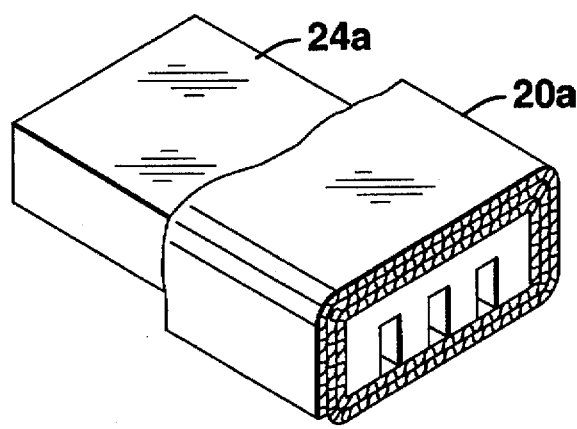
FIG_4
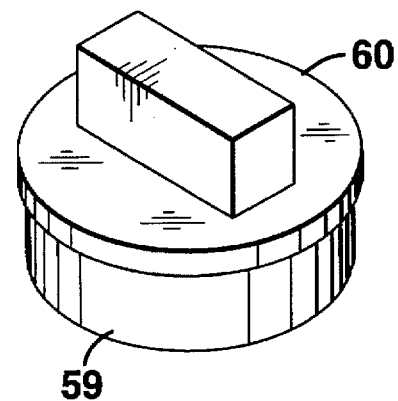
FIG_6
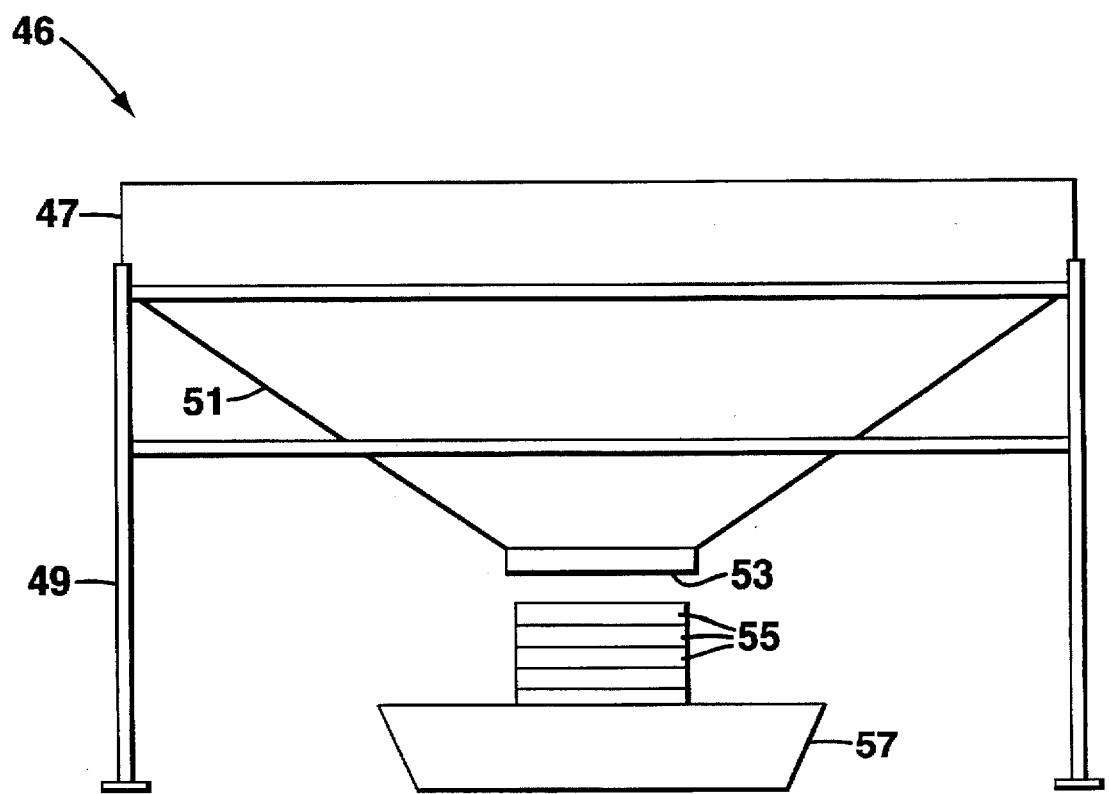
FIG_5

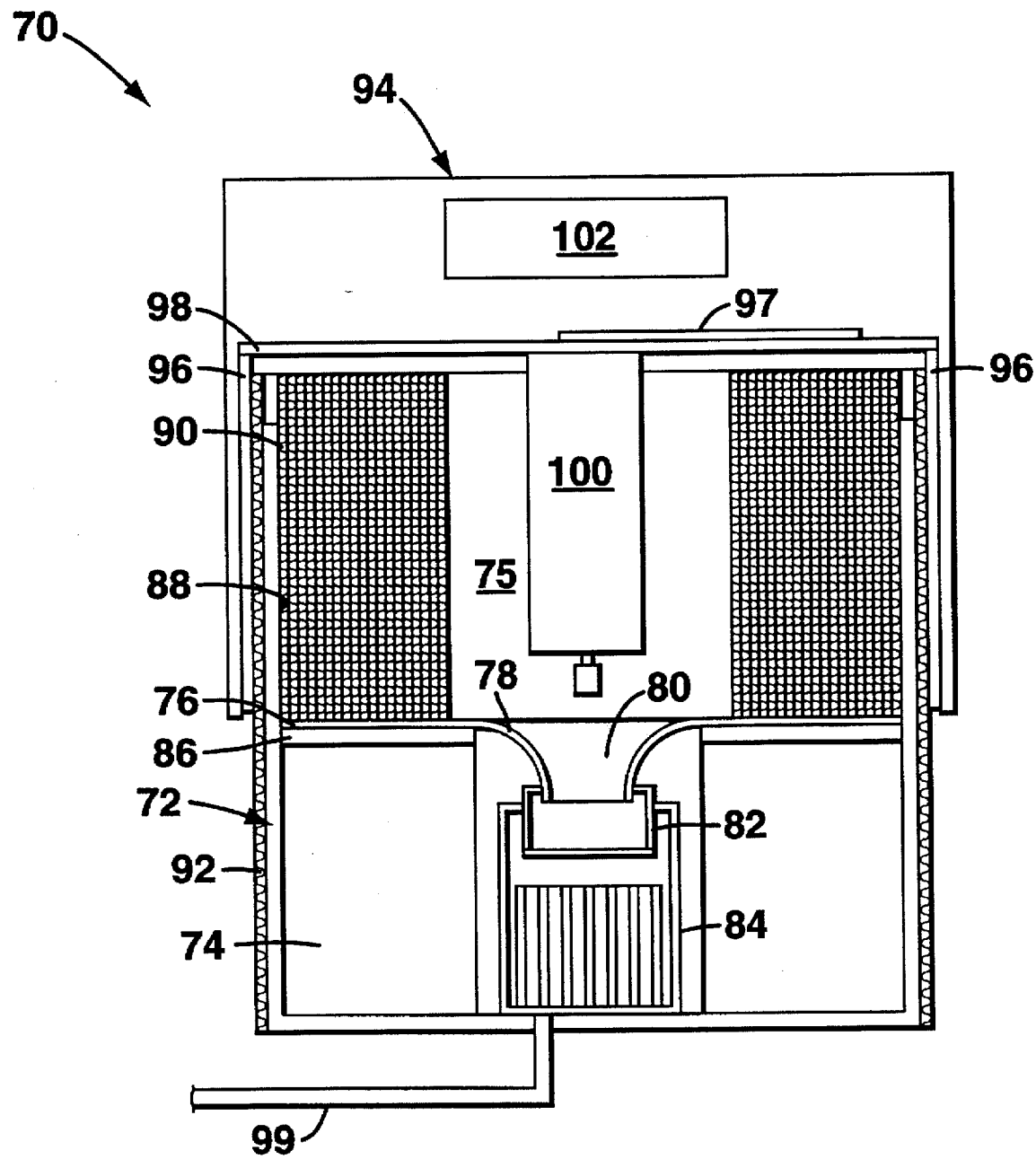
FIG_7

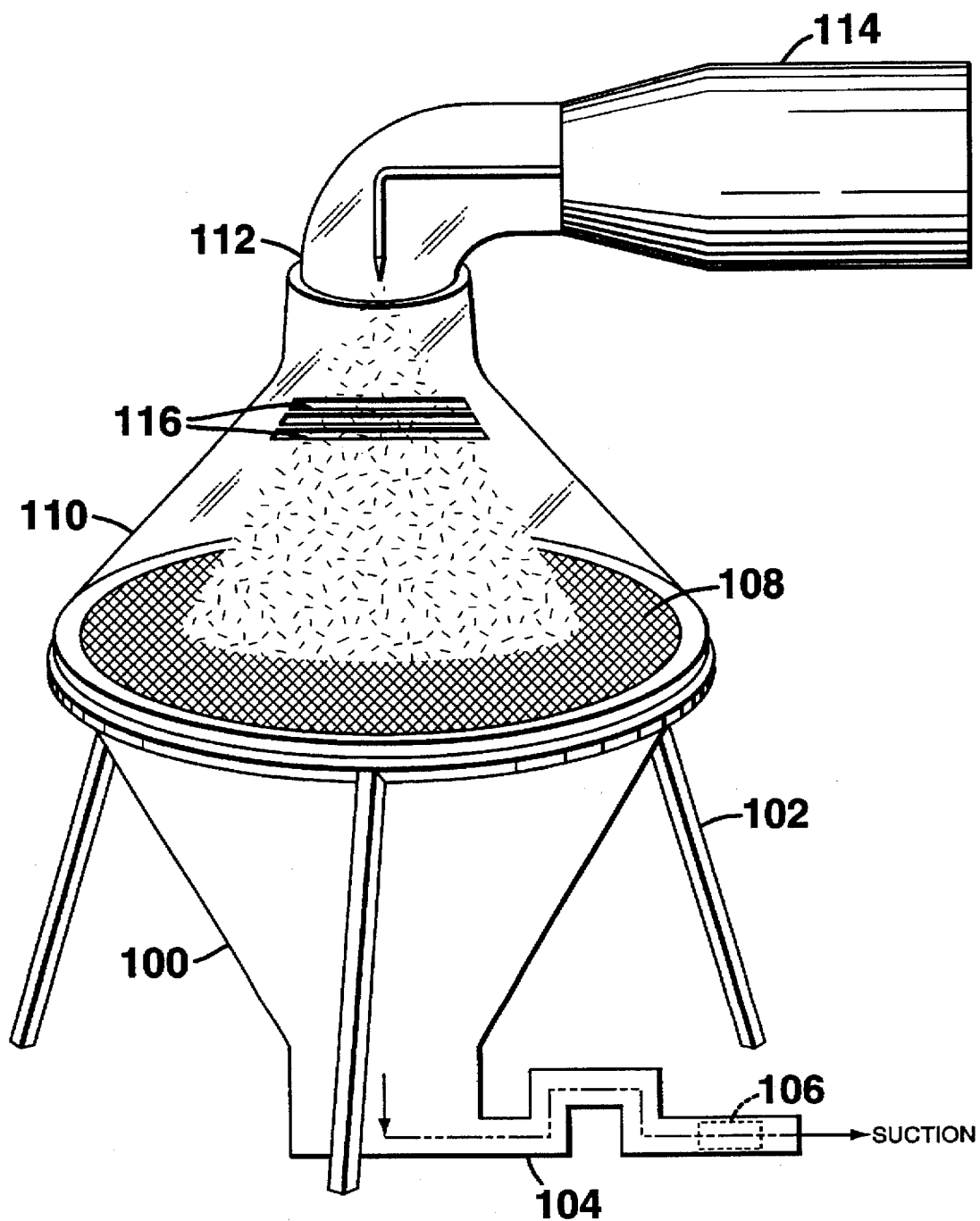
FIG_8

5,676,960

COMPOSITION FOR TREATING INSECTS

This is a Rule 60 Division of application, U.S. Ser. No. 08/414,141 filed Mar. 30, 1995, now U.S. Pat. No. 5,609,879 which is a Rule 62 Continuation of U.S. Ser. No. 08/022,043 filed Feb. 24, 1993, now abandoned.

FIELD OF THE INVENTION

The present invention relates to method, compositions and apparatus for treating a population of social insects.

BACKGROUND OF THE INVENTION

High populations of many insects are considered a pest by man and attempts are made to control the populations. Large populations may be a public health or simply nuisance factor, as, for example, with ants or wasps, or may actually cause physical damage to property, as for example, with termites. Many attempts have been made in the past to treat an insect population with a toxic material to control the population.

On the other hand, high populations of some insects, such as honey bees, are considered beneficial and it is desirable to treat such populations to maintain their health and control disease within the population.

PRIOR ART

The most common method in practice today for the control of insects is the use of fast-acting contact insecticides. Thus for example to control subterranean termites such chemicals are used to create a chemical barrier in the soil. By this method, the soil around a structure is drenched with a 1% emulsion of a fast-acting toxicant that kills termites on contact. Soil termiticides of this type are persistent, meaning that they do not break down readily in the soil and retain the toxic effect for many years. Although generally effective the major drawback of this method is the environmental contamination resulting from the necessarily large gallonages required to drench all the soil surrounding the foundation of a house.

A further method of dispersing an active ingredient within a population is to utilize a bait which is treated with the active ingredient. The insect ingests the bait and, if the active ingredient is toxic, the insect is poisoned.

Some insects, notably termites, ants, wasps, honey bees and, to a certain extent, cockroaches, exhibit a social behaviour that includes grooming, trophallaxis, (exchange of gut content) antennation and palpation. Social insects as used herein therefore shall mean those insects which live in colonies and exhibit characteristics of grooming and/or trophallaxis. These social habits of the insects may lead to transmission of the active ingredient throughout the population. As such, the kill ratio, that is, the ratio of the number initially contacting the toxicant to the number killed, is increased.

Baiting has been the main focus of research aimed at control of social insects. Baiting involves the incorporation of the slow acting toxicant in the feeding substrate at a concentration which is non-repellant to the insect. The drawbacks of baiting are many: 1) The insects may not find the bait 2) the number and volume of baits is often small compared to other available and pre-established feeding sources 3) the concentration which is non-repellent is usually below 1000 ppm and often in the range of 100 to 10 ppm, which leads to small oral dosing and low potential for lethal transmission via exchange of gut content (trophallaxis) 4) for social insects such as termites and ants which encounter the baits via trials and tunnels, dead accumulating in the vicinity of the bait can inhibit further visitation at the baits, 5) too few visit the baits to have a substantial effect on the population, and 6) baits may degrade in the field thus losing their attractiveness or toxicity. Research has focused on addressing these many problems for various pests.

Baiting has been the major focus of subterranean termite control research since 1961 when Esenther et al reported the attractancy of fungus infected wood to termites (Science 34:50). The earliest success against termites was reported in 1968 when Esenther and Gray (Can. Entomol. 100:827–834) reported effective suppression using mirex impregnated attractant wood blocks. The objectives of this research have been to 1) identify suitably slow acting toxicants 2) to determine suitable non-repellent concentrations of toxicants in bait substrates, and 3) to identify convenient and attractive feeding substrates.

After mirex was banned several other slow-acting compounds were evaluated (Su & Scheffrahn, 1991, USDA F.S. Gen. Tech. Rep. PWS-128:51–57) and the following potential bait toxicants identified: amidinohydrazones, e.g., hydramethylnon (Amdro), avermectin B1, A-9248, sulfluramid, and the insect growth regulators: methoprene, fenoxycarb, and S-31183. French (1991) (IRG/WP/1503) also reported silafluofen, glycol borate esters, and dihaloalkyl arylsulfone.

Bait substrates have included sweetgum, *Liquidambar styraciflua*, wood blocks decayed with the brown rot fungus, *Gleophyllum trabeum*, (Esenther and Beal, J. Econ. Entomol. 71:604–607); paper pulp sandwiched between corrugated boxboard (Esenther, 1985), sawdust rotted with *Tremella fuciformis* and sawdust+3% agar+bagasse powder (Gao, 1987, Biol. and Contr. Formosan Sub. Termite, Univ. Hawaii), decayed tulip tree wood blocks (Beal, 1974, Conn. Agric. Expt. Stn. Bull. 748), grass baits used for harvester termites (Duncan et al 1990, Bull. Ent. Res. 80:277–287), well rotten pine wood (Logan and Abood, 1990, Bull. Ent. Res. 80:19–26), oven-dried pine board (Su et al, 1991, J. Econ. Entomol. 84:1525–1531) toilet paper rolls (Haverty et al 1975), cardboard and cork (French et al, 1986, Sociobiology 11:303–309).

It is a prerequisite that the insect receives a sufficient dosage of the active ingredient to be effective. One reason for utilizing an active ingredient in a bait is that if the bait is attractive, the insect is likely to repeat feeding at the bait and therefore will receive the required dosage. However, it has been found that the presence of high dosages of active ingredient in the bait can act as a repellant for the insect so that they are discouraged from partaking of the bait. This means that the dosage in the bait has to be reduced and therefore the treatment time increased.

Reported results show that bait acceptance threshold concentrations (BATC) for various slow-acting toxicants when used with termites are as follows:

| Toxicant | Termite | BATC (ppm) | Author |
| --- | --- | --- | --- |
| A-9248 | Coptotermes formosanus | 600 | Su & Schf, 1991 |
| mirex | Coptotermes formosanus | 90 | Su & Schf, 1991 |
| sulfluramid | Coptotermes | 10 | Su & Schf, |

-continued

| Toxicant | Termite | BATC (ppm) | Author |
|---|---|---|---|
| | formosanus | 1991 | |
| mirex | Reticulitermes flavipes | 15 | Su & Schf, 1991 |
| sulfluramid | Reticulitermes flavipes | 30 | Su & Schf, 1991 |
| Ba metaborate | Reticulitermes flavipes | 5000 | Grace, 1990 |
| fenoxycarb | Reticulitermes spp. | 1000 | Jones, 1988 |
| Ro16-1295 | Reticulitermes spp. | 1000 | Jones, 1988 |
| Avermectin $B_2$ | Reticulitermes spp. | 1000 | Jones, 1988 |
| Tim-Bor | Coptotermes formosanus | 1800 | Su & Schf, 1991 |
| Tim-Bor | Reticulitermes flavipes | 450–900 | Su & Schf, 1991 |
| Avermectin | Reticulitermes flavipes | 50 | Esenther, 1985 Su et al, 1982 |
| Amdro | Coptotermes formosanus | 1000 | |

It can be seen from the above table that bait acceptance threshold concentrations for most slow acting toxicants range from 10 to 5,000 ppm, which for most toxicants is less than one order of magnitude above the concentration that will kill the termite.

To help assess the effect of the range of suitable concentration of bait acceptance Su & Scheffrahn (1991) defined a useful index for the evaluation of potential bait toxicants: the Bait Toxicant Efficacy Index is defined as the bait acceptance threshold concentration (BATC) divided by the delayed mortality threshold concentration.

The highest recorded BTE was 9 for the toxicant A-9248. In other words, the minimum amount that is toxic for all slow-acting materials tested against termites, is less than 10 times the maximum amount they will feed upon. Therefore, not only are the effective bait concentrations very low but also the working range is very narrow which restricts bait efficacy in the field.

Attempts have also been made to apply toxicants as a dust to the insects. In dusting, the toxicant is applied as a dust or with dust diluents in dry areas where the insects are likely to be found. For insects which engage in social contacts there is the possibility of transfer from those that contact the dust to others via such interactions as mating, antennation, palpation, or grooming. Dusting can be either indirect (the insect's environment, nest, or galleries) or direct (the insects themselves). Among the drawbacks of dusting are that they 1) often cannot be put where the insects will encounter them 2) they fail to cling to insect cuticular surfaces under damp conditions 3) they come off too quickly simply by movement and abrasion in the microhabitats of the insects 4) they are too easily self groomed thus too rapidly intoxicating the dusted insects and leaving less for undusted insects to acquire, and 5) there are relatively low rates of effective lethal transfer between individuals (e.g. 1:10). Thus in practice dusts have only been found to be effective with dry-wood termites which have small populations (10,000 or fewer), in confined colonies, with dry galleries in wood. Dusts have not proven effective with the more important subterranean termite pests which have colonies of several million occupying extensive foraging territories in the soil.

The concept of applying toxic dusts for control of termites was discussed in detail by Randall and Doody, 1934, *Termites and Termite Control*, Univ. Calif. Press. They evaluated a wide variety of inorganic compounds and compared them in terms of hours to kill 80%. They envisioned application with dust guns into the termite galleries followed by contact toxicity and also inter-termite transmission via grooming from dusted cuticular surfaces. They stated that dusting is limited in effectiveness to wood-inhabiting termites (damp-wood and dry-wood termites) and was an inadequate means of control for subterranean termites due to dampness of the galleries which resulted in "caking" of the toxicants and therefore prevented dispersion in the population. More recently there have been claims that dusting could work with some toxicants, namely mirex or arsenicals (arsenic trioxide), with some species of subterranean termites (*Mastotermes darwiniensis* and some Coptotermes spp.) (Lin, 1987. *Biol. & Control of Formosan Sub. Term.* Univ. Hawaii,; French, 1991. IRG/WP/1503). French described the trapping of a portion of the population in cardboard traps, directly dusting them (rather than the galleries) and returning them into the colony of origin. Grace and Abdallay, 1990, J. Appl. Ent. 190:283–288; evaluated boron dusts for such application and also noted that trapping about 10% of the population would be required for dusts to work at the kill ratios (1 dusted to 10 killed) they observed in small soil containers. Esenther 1985 (IRG/WP/1257) evaluated Avermectin applied to silica carrier dust at the rate of 0.5 ug/mg dust. French (1991) (IRG/WP/1503) has also referred to the use of spores of the pathogenic fungus *Metarhizium unisopliae* as a dust toxicant. Su and Scheffrahn (1992) suggested that toxicants could be incorporated in "tracking powder" which would be distributed among termites by contact and grooming acquisition. Myles and Grace (1991) reported that due to rapid rates of dust loss on moist soil that effective treatment would require that about 20% of the population be trapped and dusted.

In order to address the problems inherent with dusting, the present applicant attempted to improve adhesion of an inorganic toxic dust (Tim-Bor) by first applying a marker pen ink to the termite to mark the termite and subsequently applying the dust before the ink dried. As reported in an article entitled "Behavioral Ecology of the Easter Subterranean Termite in Ontario as a Basis for Control" delivered at a conference, November, 1991 in Toronto, this technique was unable to effectively mark and dust large numbers of insects. The applicant also reported that spray paints aided the adhesion of the Tim-Bor dust and that maximal loading was obtained with two or three cycles of spraying followed by dusting. Although this proved a more effective application technique, and further improvements in ease of application were speculated by incorporating the toxicant into the aerosol, the kill ratio still did not exceed 1:20, indicating no great improvement over dusting alone.

It is therefore an object of the present invention to provide method, apparatus, and a composition for treating insect population that utilizes the social habits of the insects and in which the above disadvantages are obviated.

SUMMARY OF INVENTION

The present invention is based upon the recognition that the potential for transmission of the active ingredient via social behaviours is greatly enhanced by providing a composition that is adhesive to the cuticle and yet removable from the cuticle by oral grooming (licking). It was further recognized that for such a composition to be effective it would have to be compatible, in numerous respects with the insect's normal behaviour and the insect's microhabitat. Thus the method of the present invention contemplates applying a composition comprising an active ingredient and a carrier which, upon application, provides a subtantially groomable, cuticle-adherent coating to the insect. Preferably, the composition provides a substantially nonmobility impending, non-irritant, non-contact-toxic, non-tacky, water-resistance coating so that the coating remains compatible with the environment and normal social behaviour of the insect.

In contrast to the spray paints previously tested, the compatibility and groomability of the coating substantially enhances transfer of the active ingredient by ingestion to other members of the colony and subsequent transmission via trophallaxis through the population. At the same time, the high loss of active ingredient experienced with dusting is avoidable.

The method of the present invention has been found particuarly useful in controlling or suppressing insect populations, most particularly subterranean termites. Most surprisingly it has been found that dosages of active ingredient several orders of magnitude higher than the BATC previously reported will be tolerated, groomed, and ingested. Consequently, kill ratios up to 1:2000 have been observed. This substantial increase in kill ratio efficiency implies a reduction in requisite trapping which in turn substantially favours commercial feasibility.

It is preferred that the active ingredient is a slow acting organic and that the carrier provide progressive release of the active ingredient as it passes through the gut of the insect. In this way, secondary and tertiary ingestion may be achieved by trophallaxis.

It is also preferred that the carrier comprises a synthetic or natural resin, an adhesive, or a film forming compound which exhibits the physical characteristics necessary to permit grooming when dry. The carrier should remain adhered to the insect yet be frangible so as to be removed in pieces. Preferably the carrier initially is maintained in solution by a solvent which will evaporate from the composition under ambient conditions causing the carrier to solidify.

It is preferred that the carrier provides a composition that is air dryable and that dries to a non-tacky surface.

It is also preferred that the carrier not induce agonistic interactions among the target insect population after application and after drying.

It is also preferred that the coating does not hinder mobility and remains adhered during locomotion.

Optionally, the composition can include one or more of the following ingredients: a substance for attracting the targeted social insect to the composition and/or for stimulating the grooming of the composition from the insect to which it is applied, a substance for modifying the water-solubility of the composition, a dye for enhancing the visibility of the composition on the insects to which it is applied, a thickening agent, or other modifying agents.

Toxicants or insecticides which exhibit the following properties are useful in the present invention. The toxicant should be slow acting, i.e., the toxicant should not kill the insect to which it is applied immediately upon contact, but, rather should kill the insect only after a period of time sufficient for the insect to transfer the toxicant to other members of the colony. The toxicant should have a mode of action of killing the target insect by ingestion. Furthermore, the toxicant must not induce excessive agonistic behaviour in the insects to which it is applied or in insects which interact with the treated insect, i.e., the toxicant should not induce the insects to which it is applied to kill so many other treated insects that the treated insects do not have a sufficient opportunity to transfer the toxicant to other members of the colony and the toxicant should not induce the insects which interact with treated insects to kill the treated insects before the treated insects have a sufficient opportunity to transfer the toxicant to other members of the colony.

Examples of toxicants which are useful in the present invention include organic compounds such as fluoroaliphatic sulfonamides such as sulfluramid and their related sulfonic acid analogues; amidinohydrazones such as hydramethylnon; avermectin, A-9248, silafluofen, glycol borate esters, dihaloalkyl sulfones, mirex; insect growth regulators such as methoprene, fenoxycarb, S-31183; and inorganics such as arsenicals, borates such as boric acid, disodium octaborate tetrahydrate, and zinc borate; and barium compounds such as barium metaborate monohydrate; and propagules of pathogens such as conidia of *Metarhizium anisopliae* and *Beauvaria bassiana*.

Carriers which exhibit the following properties are useful in the present invention. When the insects' habitat is humid, the carrier should be water-resistant. The carrier must adhere sufficiently to the insect to which it is applied that it is not substantially removed from the insect by abrasion resulting from the normal locomotion of the treated insect. The carrier must be groomable from the treated insect by other members of the colony, i.e., the carrier must be sufficiently soft, brittle or frangible after drying that it can be removed in fragmentary fashion, i.e. in fragments smaller than the total coating, from an insect to which it has been applied specifically by the oral grooming activities (not simply by casual contact, palpation or antennation) of other members of the insect colony. The carrier should be substantially non-toxic upon contact with the insect to which it is applied, i.e., the toxicant must exhibit delayed toxicity with the treated insect. The carrier should not overly inhibit the normal locomotion of the insect to which it is applied, i.e., the carrier must not so hinder the locomotion of the treated insect that the treated insect cannot disperse from the release site back into the galleries, tunnels or nest of the colony. The carrier should preferably solidify to a substantially nontacky state under ambient conditions. The carrier must not chemically inactivate the toxicant which is dissolved or suspended therein so that the toxicant will be available for killing the targeted insect when the compositions is ingested by a member of the targeted insect colony. Carriers which are useful in the present invention include synthetic resins, in particular, hydrocarbon formaldehyde resins, more particularly phenolic formaldehyde resins. Particularly preferred are resins in the classification UCAR CK21200-2500, especially CK2103. As will be understood by those skilled in the art, examples of other carriers useful in the present invention when exhibiting the desired characteristics include high softening point resins, other phenolic resins, such as bis phenol-A, maleic anhydride/phenolic adducts; amino resins, such as urea-formaldehyde and melamine-formaldehyde, ethyl cellulose, shellac, milk products, casein, albumin, glutin, malrodextrins, sugars, starches and derivatives, gums, such as acacia, guar and xanthan, alginates, wood derivatives, such as gum rosin and wood rosin, alkyd resins, polyvinyl alcohol (PVA), polyvinyl chloride (PVC), CPC, acrylic polymers and copolymers, N-substituted pyrrolidones, and waxes, such as bees wax and paraffin.

The carrier is preferably maintained in solution by a solvent prior to application. Solvents which exhibit the following properties are useful in the present invention. The solvent should evaporate substantially from the composition of the present invention under ambient conditions and should not itself be toxic to the insect. Examples of solvents which are useful in the present invention include alkanes, alcohols such as n-propyl alcohol, n-butyl alcohol, ehtyl alcohol glycols and their derivatives; glycerols and their derivatives; and ketones, such as diacetone alcohol.

When included in the composition, attractants which exhibit the following properties are useful in the present invention. The attractant should attract insects from the targeted colony to treated insects so that they will have an opportunity to groom the treated insects. Attractants which are useful in the present invention for specific social insects include diacetone alcohol, extracts of sweet gum and pine wood, extracts of wood rot fungi such as *Gleophylum trabeum* and *Tramella fuciformis*; alpha and beta pinenes, and (Z.Z.E)-3,6,8-dodecatrien-1-ol, and insect cuticular hydrocarbons such as $C_{20-40}$ alkanes, monomethylalkanes and monoalkenes, particularly for subterranean termites. For other social insects' trail, sex aggregation phermones and phagostimulants may be useful.

Water-proofing agents which may be useful in the present invention include the above resins as well as silicone polymers, fluorocarbon resins, and polyvalent cations of fatty acids, such as magnesium stearates, and para-nonylphenol.

Thickening agents may be useful in the present invention to improve loading of the insect and inhibit excessive spreading. Suitable thickening agents include derivatized cellulose, such as methylcellulose, gums, derivatives of acrylic acids, hydroxyethylcellulose, cellulose powder, talcum powder, charcoal powder, plaster of Paris and clay.

Compositions in accordance with the present invention can be dispensed as an aerosol using a suitable propellant. Examples of propellants which are useful in the present invention include nitrogen, carbon dioxide and nitrous oxide. Examples of liquified gases which are useful in the present invention include n-butane, iso-butane, n-propane, dimethylether, chlorofluoromethane, difluoroethane and chlorodifluoroethane. In addition to standard aerosol delivery systems, aerosol compositions may be prepared and dispensed through barrier pack systems. Examples of these systems include products with the trade names seprocontainer, mira-flo, powder-flo and innovain.

The present invention seeks to deliver as much toxicant into the colony population as possible so that it can be passed from colony member to colony member by secondary and tertiary trophallaxis of gut contents. Therefore, it is useful to combine as much toxicant as the carrier can dissolve or suspend without overly increasing the viscosity of the composition or causing the composition to cake so that it cannot be applied to the target insect. The relative amounts of the toxicant and the carrier which can be used in the present invention will vary depending upon the specific materials used and the target insect. It has been found that a much higher range of toxicant concentrations can be orally ingested via grooming of the dried composition (up to 950,000 ppm) in comparison to the concentrations ingested in baits (less than 5,000 ppm for termites). However, it has been found that amounts of toxicants between approximately 1% and 67% by weight are useful in the present invention; particularly between approximately 10% and 50% by weight, most preferably between approximately 25% and 40% by weight. Amounts of solvent which are useful in the present invention are between approximately 30% and 92% by weight; preferably between approximately 40% and 75% by weight. Amounts of resin which are useful in the present invention are between approximately 1% and 10% by weight; preferably, between approximately 2% and 7%. Amounts of attractant which are useful in the present invention are between approximately 0% and 1% by weight; preferably, between approximately 0% and 0.2%. Amounts of water proofing agent which are useful in the present invention are between approximately 0% and 1% by weight; preferably, between approximately 0% and 0.2%. Amounts of thickening agent which are useful in the present invention are between approximately 0% and 75% by weight depending on the solubility of the active ingredient. Amounts of dye which are useful in the present invention are between approximately 2% and 8% by weight; preferably, between approximately 5% and 7%.

BRIEF DESCRIPTION OF THE DRAWINGS

Embodiments of the apparatus of the present invention and the methods and compositions used with that apparatus will now be described by way of example only and with reference to the accompanying drawings, in which:

FIG. 1 is a schematic representation of a typical treatment area;

FIG. 2 is a perspective view of a trap utilized in the treatment area shown in FIG. 1;

FIG. 3 is a section to an alternative form of trap utilized in the treatment area shown in FIG. 1;

FIG. 4 shows an alternative form of trap utilized in the treatment area of FIG. 1;

FIG. 5 shows an apparatus separating termites from the traps;

FIG. 6 is a representation of an applicator;

FIG. 7 shows an alternative form of trap that may also be used to treat collected insects; and FIG. 8 shows an apparatus for applying a composition to a collected portion of a colony.

COLLECTION AND RELEASE

Referring therefore to FIG. 1, a treatment area generally indicated as 10 includes a number of collection sites 12 located on or below the surface of the ground. The traps 12 are interconnected by cardboard tubing to facilitate passage of the selected insects to an aggregating trap 16. The most suitable location for the traps is determined by visual inspection of the site to locate the foraging areas of the termites.

As can be seen in FIG. 2, each of the traps 12 consist of a plastic PVC cylinder 18 within which is rolled an elongate strip of corrugated cardboard 20. The corrugations 22 of the cardboard 20 provide longitudinal passages that encourage infestation by termites. A wood block 24 is optionally located at the centre of the corrugated cardboard roll 20 to provide a reserve food supply for termites within the trap.

The trap 12 is interconnected through tubes 14, as noted above, to the trap 16. Trap 16 is shown in further detail in FIG. 3 and includes an outer housing 26 through which the tubing 14 may pass with a water reservoir 28 at the base. The water reservoir is embedded in a sand barrier 30 and is connected to the surface through a fill tube 32. A layer of fine sand 34 is placed over the sand barrier 30 to promote movement of the moisture from the reservoir 28 into a coarser sand layer 36.

A replaceable aggregation layer 38 is supported on the sand layer 36 and consists of horizontal pieces of plywood 40 separated by battens 42. A corrugated cardboard strip 44 is spirally wound around the stack of plywood layers 30 to promote passage of termites into the area between the plywood layers 40.

Termites congregate in the traps 12, 14 and may be collected periodically by removal of the cardboard roll 20, or aggregation layer 38. These may then be replaced by new rolls or layers as necessary.

An alternative trap to that shown in FIG. 2 is shown in FIG. 4 which utilizes an elongate grooved board 24a encased with cardboard 20a to promote aggregation of the termites. The elongate dimensions promote rapid interception by the target insects.

Upon collection, the termites have to be separated from the cardboard 20,44 so that they may be treated. The separation is accomplished through means of a separator 46, shown in FIG. 5, comprising a screen 47 supported on legs 49 and having a conical funnel 51 extending to an outlet 53. The outlet 53 is aligned over a plurality of sieves 55 which allow separation of the cardboard and debris from the termites. The termites are collected in a collecting box 57 from where they can be removed for subsequent treatment.

Treatment of the insects is by application of a composition containing an active ingredient and a carrier to the dorsal area of the insect. Application can be by any of various means but preferrably either with a blotter-type applicator, FIG. 6, or a spray applicator and spray chamber, FIG. 8.

After treatment, the insects are released into the population to disseminate the active ingredient. The provision of multiple traps facilitates the re-introduction of treated termites by allowing their release throughout the colony. This enhances distribution of the active ingredient in a rapid and efficient manner. The cardboard tubing and elongate cardboard wrapped boards of the trapping system also serve at this juncture in promoting the rapid movement of treated termites from the release sites back into the less accessible recesses of the foraging territory.

THE COMPOSITION

As noted above, certain insects exhibit a social behaviour. Such insects include truly social bees ants, wasps and termites and subsocial insects such as cockroaches. In order to take advantage of the social grooming habits of insects to be treated, it is necessary that the composition exhibit good adherence and yet remain groomable by other insects. Moreover, the composition must contain a sufficient dosage of active ingredient to provide the requisite kill ratio. Because of the environment in which such insects live, it is preferable that the composition is water resistant.

It has surprisingly been found that the dosages of active ingredient that may be applied to the exterior of an insect are significantly higher than those that will be tolerated in a bait. Moreover, concentrations that are not acceptable when included in a bait are actively groomed and ingested when applied topically. The carrier should also be compatible with the insect to be treated. In the case of a termite, the skin is a wax like substance with low melting point. Accordingly solvents of cuticular waxes such as low molecular weight alcohols promote spreading and good adherence.

To facilitate application, the composition is preferred to be in liquid form and maintain the active ingredient in suspension or solution. The carrier is preferably air dryable and, upon evaporation of solvents, leaves a non-tacky, groomable coating containing the active ingredient. The composition should be applied topically and accordingly the viscosity of the composition may be increased by admixture of a suitable thickening agent. This ensures that the composition does not spread excessively beyond the area where it is applied. A carrier including a resin which is maintained in solution by solvents that evaporate at normal ambient temperatures is preferred. In particular, resins that are alcohol soluble are preferred. It is also preferred that the carrier promotes grooming by other members of the population and therefore a carrier including an attractant is preferred.

Suitable carriers have been found to include a curable resin maintained in solution by suitable solvents. It is preferred that the solvents are solvents for resins and waxes. Suitable resins may include phenolic resins, maleic anhydrides, ethyl cellulose and shellac. In general it is believed that hydrocarbon-aldehyde resins are suitable and phenol-formaldehyde resins are preferred, particularly Bakelite Phenolic Resins CK 2100–2500 series, especially, CK-2103. Suitable solvents include n-butanol, n-propanol and diacetone alcohol, ethyl alcohol or a mixture of two or more of such solvents.

Suitable carriers have also been found to contain a small amount of silicone which is believed to enhance the water resistance of the composition. It is also noted that diacetone alchohol is an attractant for certain insects, particularly bark beetle, this may enhance the grooming of the composition by other members of the population. It has been found that suitable solutions of carriers that provide the requisite physical properties for the composition include inks, such as those used in permanent marker pens.

An ink that has been tested successfully as a carrier has a composition of:

| | % BY WT. | CAS. # | OTHER IDENTIFIER |
| --- | --- | --- | --- |
| n-butanol | 21 | 71-36-3 | |
| diacetone alcohol | 25 | 123-42-2 | |
| n-propanol | 42 | 71-23-8 | |
| phenolic resin | 5 | | UCAR CK-2103 |
| silicone | 0.1 | 67762-85-0 | |
| dye (approx) | 7 | | CI solvent red 109 |

Similar compositions are used with different dyes for different colored inks. The phenolic resin is a phenol formaldehyde resin.

Initial testing involved screening of various toxicants in a 50% concentration (0.5 g/1 ml ink) in the above ink at a ratio of 1 treated termite to 10 untreated termites in petri dish tests. The application was made by absorbing a 2 ml puddle of the composition onto the sponge and then gently pressing the wet sponge surface to the dorsal surface of groups of several hundred termites in a 6.5 cm dish lined with paper. The paper provided a gripping surface so that the termites resisted sticking to the sponge. After treatment, the termites were knocked onto dry brown paper towels in large containers to dry for one hour prior to transfer to the test dish. The results are set out in Table I below:

TABLE I

| Toxicant | LT90 (days) | % Mortality (day 46) |
| --- | --- | --- |
| Sulfluramid | less than 10 | 100 |
| Zinc borate (fine) | 14 | 100 |
| Barium metaborate | 16 | 100 |
| Boric Acid | 25 | 100 |
| XPI-174 inorg. borate | 19 | 98 |
| Tim-Bor | 22 | 99 |
| Na hexafluorisilicate | — | 85 |
| Borax | — | 75 |
| Chlortetracycline HCl | — | 65 |
| Resin control | — | 35 |
| Sodium fluoride | — | 33 |
| Barium fluoride | — | 32 |
| Untreated control | — | 20 |

From this test it was noted that sulfluramid (available from Griffin Corporation, Valdosta, Ga.) produced a more rapid kill than the borates. Sulfluramid and the borates demonstrated kill potential at 1:10 while some toxicants failed to achieve such a kill potential. Subsequent tests indicated maximum kill ratios with borates around 1:20.

The superior performance of sulfluramid suggested that other organic slow acting toxicants might be particuarly effective. Hydramethylnon was therefore tested at 50% concentration with results given in Table IA below.

TABLE IA

| | | | Avg. % Mort./reading | | | |
|---|---|---|---|---|---|---|
| | | Date/92 | Oct 20 | Oct. 27 | Nov. 2 | Nov. 9 |
| # | # Treated | # Untreated | 0 | 8 | 13 | 20 |
| 1 | 10 | 90 | 0.00 | 100.00 | 100.00 | 100.00 |
| 2 | 5 | 95 | 0.00 | 100.00 | 100.00 | 100.00 |
| 3 | 4 | 96 | 0.00 | 100.00 | 100.00 | 100.00 |
| 4 | 3 | 97 | 0.00 | 96.75 | 100.00 | 100.00 |
| 5 | 2 | 98 | 0.00 | 25.00 | 100.00 | 100.00 |
| 6 | 1 | 99 | 0.00 | 16.75 | 81.50 | 100.00 |
| 7 | 0 | 100 | 0.00 | 2.75 | 3.75 | 4.25 |
| # | # Treated | # Untreated | 0 | 8 | 13 | 20 |

These petri dish tests indicated a kill ratio of 1:99. However, subsequent tests in soil cups comparing sulfuramid and hydramethylnon indicated that sulfuramid achieved a kill ratio of 1:250 whereas hydramethylnon achieved a kill ratio of about 1:60 (Table IB).

TABLE IB

DATE: 15 February 1993  Days After = 80
SULFURAMID (75%)     # Alive

| # | Ratio | ADDED | A | B | C | Avg Alive | Avg % Mort | STD |
|---|---|---|---|---|---|---|---|---|
| 1 | 1:1000 | 1 | 826 | 720 | 482 | 676.00 | 32.47 | 143.84 |
| 2 | 1:500 | 2 | 186 | 173 | 644 | 334.33 | 66.63 | 219.03 |
| 3 | 1:250 | 4 | 24 | 1 | 8 | 11.00 | 98.90 | 9.63 |
| 4 | 1:167 | 6 | 0 | 0 | 0 | 0.00 | 100.00 | 0.00 |
| 5 | 1:125 | 8 | 0 | 0 | 0 | 0.00 | 100.00 | 0.00 |

HYDRAMETHYLNON (50%)     # Alive

| # | Ratio | ADDED | A | C | C | Avg Alive | Avg % Mort | STD |
|---|---|---|---|---|---|---|---|---|
| 6 | 1:1000 | 1 | 752 | 772 | 829 | 784.33 | 21.65 | 32.62 |
| 7 | 1:500 | 2 | 694 | 773 | 560 | 682.33 | 31.90 | 79.22 |
| 8 | 1:250 | 4 | 712 | 681 | 564 | 652.33 | 35.03 | 63.73 |
| 9 | 1:167 | 6 | 767 | 660 | 750 | 725.67 | 27.67 | 46.95 |
| 10 | 1:125 | 8 | 0 | 711 | 756 | 489.00 | 51.49 | 346.26 |

CONTROL     # Alive

| # | Ratio | ADDED | A | C | C | Aug Alive | Aug % Mort | STD |
|---|---|---|---|---|---|---|---|---|
| 11 | 1:125 | 8 | 786 | 627 | 791 | 734.67 | 27.12 | 76.16 |

Further petri dish tests with sulfluramid indicated kill ratios in excess of 1:500 with extended lethal times at higher test ratios as shown in Table II.

TABLE II

| Ratios Tested (Treated:Untreated) | | | Lethal Time (days) | | | |
|---|---|---|---|---|---|---|
| 1st | 2nd | 3rd | $LT_{50}$ | | $LT_{90}$ | |
| Test | Test | Test | Observed | interpolated | Observed | interpolated |
| 1:4 | | | 3 | 3 | 7 | 7 |
| 1:9 | | | 4 | 4 | 8 | 8 |
| 1:13 | | | 7 | 5 | 12 | 10 |
| 1:16 | | | 4 | 5 | 10 | 10 |
| 1:19 | | | 7 | 6 | 11 | 11 |
| | 1:20 | | 6 | 6 | 9 | 12 |
| 1:24 | | | 6 | 6 | 10 | 12 |

TABLE II-continued

| Ratios Tested (Treated:Untreated) | | | Lethal Time (days) | | | |
|---|---|---|---|---|---|---|
| 1st | 2nd | 3rd | $LT_{50}$ | | $LT_{90}$ | |
| Test | Test | Test | Observed | interpolated | Observed | interpolated |
| 1:32 | | | 6 | 7 | 13 | 13 |
| | 1:40 | | 7 | 7 | 10 | 14 |
| 1:49 | | | 8 | 8 | 15 | 15 |
| | 1:60 | | 6 | 8 | 14 | 16 |
| | 1:80 | | 9 | 9 | 17 | 17 |
| 1:99 | | | 9 | 9 | 13 | 17 |
| | 1:100 | | 9 | 9 | 15 | 17 |
| | 1:120 | | 9 | 10 | 18 | 18 |
| | 1:140 | | 19 | 11 | 30 | 20 |
| | | 1:150 | 22 | 13 | 49 | 22 |
| | 1:160 | | 14 | 15 | 22 | 25 |
| | 1:180 | | 15 | 17 | 20 | 27 |
| | 1:200 | | 24 | 19 | 36 | 29 |
| | | 1:200 | 19 | 19 | 45 | 29 |
| | | 1:250 | 20 | 21 | 43 | 31 |
| | | 1:300 | 23 | 25 | 34 | 35 |
| | | 1:350 | 30 | 27 | 34 | 37 |

TABLE II-continued

| Ratios Tested (Treated:Untreated) | | | Lethal Time (days) | | | |
|---|---|---|---|---|---|---|
| 1st | 2nd | 3rd | $LT_{50}$ | | $LT_{90}$ | |
| Test | Test | Test | Observed | interpolated | Observed | interpolated |
| | | 1:400 | 31 | 30 | 40 | 40 |
| | | 1:450 | 33 | 33 | 43 | 43 |
| | | 1:500 | 35 | 35 | 43 | 45 |

To test the efficacy of the sulfuramid-ink composition under more realistic conditions, a "house unit" experiment was devised. In this test a realistically large population of termites (50,000) was established on soil trays surmounted by a wood structure simulating the basic elements of wood-frame construction. Two exemplary compositions were prepared using technical sulfluramid as an active ingredient and an ink having the composition set out above as carrier. Each was applied with a latex cosmetic sponge approximately 1 cm thick by 6.5 cm diameter attached to a woodblock of a same diameter. Two compositions were prepared, one of 50% and one of 100% concentration as set out in Examples 1 and 2.

EXAMPLE I

| COMPONENT | Formulary for Cuticle-Adherent, Grooming Stimulants | PERCENT SOL | PARTS BASIS | W/W BASIS | PPHS[1] |
|---|---|---|---|---|---|
| SULFLURAMID | | 50 | 500 | 33.3% | 80.5 |
| SOLVENT | n-Butanol | 21 | 210 | 14.0% | |
| | Diacetone alcohol | 25 | 250 | 16.7% | |
| | n-Propanol | 42 | 420 | 28.0% | |
| RESIN | | 5 | 50 | 3.3% | 8.1 |
| DYE | | 7 | 70 | 4.7% | 11.3 |
| WATERPROOFER | | 0.1 | 1 | 0.1% | 0.2 |
| THICKENER | | 0 | 0 | 0.0% | 0.0 |
| ATTRACTANT | | 0 | 0 | 0.0% | 0.0 |
| | W/Volume Percent | 50.0% | | 100% | 100% |

A.I. % (W/W) 33.3%
Total Parts 1501
Total Solids 621
[1]ON A SOLIDS BASIS

EXAMPLE II

| COMPONENT | Formulary for Cuticle-Adherent, Grooming Stimulants | PERCENT SOL | PARTS BASIS | W/W BASIS | PPHS[1] |
|---|---|---|---|---|---|
| SULFLURAMID | | 100 | 1000 | 50.0% | 89.2 |
| SOLVENT | n-Butanol | 21 | 210 | 10.5% | |
| | Diacetone alcohol | 25 | 250 | 12.5% | |
| | n-Propanol | 42 | 420 | 21.0% | |
| RESIN | | 5 | 50 | 2.5% | 4.5 |
| DYE | | 7 | 70 | 3.5% | 6.2 |
| WATERPROOFER | | 0.1 | 1 | 0.0% | 0.1 |
| THICKENER | | 0 | 0 | 0.0% | 0.0 |
| ATTRACTANT | | 0 | 0 | 0.0% | 0.0 |
| | W/Volume Percent | 99.9% | | 100% | 100% |

A.I. % (W/W) 50.0%
Total Parts 2001
Total Solids 1121
[1]ON A SOLIDS BASIS

The number transferred represented 1% of the total population of insects in the test units. The results obtained are set out in Table III below.

TABLE III

Mortality in Test Units With 50,000 Reticulitermes flavipes

| Start | Treat | Trtmnt. | # Added | % Dismtld. | Days | # Alive | % Mort. | Δ Live | K:11 Ratio |
|---|---|---|---|---|---|---|---|---|---|
| 50 % Sulfuramid in Ink (0.5 gram in 1.0 ml) Applied by Blotter | | | | | | | | | |
| May 22 | Jun 3 | control | 2,500 | 5 | Jul 3 | 30 | 30,187 | | |
| May 22 | Jun 3 | trtmnt | 2,500 | 5 | Jul 3 | 30 | 0 | 100.0 | 30,187 | 1:12.0 |
| Jun 3 | Jun 11 | control | 2,500 | 5 | Jul 16 | 35 | 29,631 | | |
| Jun 3 | Jun 11 | trtmnt | 2,500 | 5 | Jul 16 | 35 | 0 | 100.0 | 29,631 | 1:11.8 |
| Jul 2 | Jul 13 | control | 2,500 | 5 | Aug 14 | 32 | 22,423 | | |

TABLE III-continued

Mortality in Test Units With 50,000 Reticulitermes flavipes

| Start | Treat | Trtmnt. | # Added | % Dismtld. | Days | # Alive | % Mort. | Δ Live | K:11 Ratio |
|---|---|---|---|---|---|---|---|---|---|
| Jul 2 | Jul 13 | trtmnt | 2,500 | 5 Aug 14 | 32 | 250 | 99.5 | 22,173 | 1:8.9 |
| Jul 10 | Jul 13 | control | 2,500 | 5 Sep 2 | 51 | 34,890 | | | |
| Jul 10 | Jul 17 | trtmnt | 2,500 | 5 Sep 2 | 55 | 0 | 100.0 | 34,890 | 1:13.9 |
| Jul 17 | Jul 24 | control | 500 | 1 Sep 2 | 40 | 23,731 | | | |
| Jul 17 | Jul 24 | trtmnt | 500 | 1 Sep 2 | 40 | 2,093 | 95.9 | 21,638 | 1:43.3 |
| Jul 25 | Jul 31 | control | 500 | 1 Sep 11 | 42 | 31,171 | | | |
| Jul 25 | Jul 31 | trtmnt | 500 | 1 Sep 11 | 42 | 0 | 100.0 | 31,171 | 1:62.3 |
| Aug 7 | Sep 9 | control | 500 | 1 Oct 27 | 49 | 20,862 | | | |
| Aug 7 | Sep 9 | trtmnt | 500 | 1 Oct 27 | 49 | 0 | 100.0 | 20,862 | 1:41.7 |
| Aug 14 | Sep 9 | control | 500 | 1 Oct 28 | 50 | 21,977 | | | |
| Aug 14 | sep 9 | trtmnt | 500 | 1 Oct 28 | 50 | 0 | 100.0 | 21,977 | 1:44.0 |
| 100% Sulfuramid in Ink (1 gram in 1 ml) Applied by Blotter | | | | | | | | | |
| Sep 1 | Sep 22 | control | 500 | 1 Nov 19 | 58 | 31,623 | | | |
| Sep 1 | Sep 22 | trtmnt | 500 | 1 Nov 19 | 58 | 484 | 99.0 | 31,139 | 1:62.3 |
| Sep 1 | Sep 22 | control | 500 | 1 Nov 19 | 58 | 26,279 | | | |
| Sep 1 | Sep 22 | trtmntl | 500 | 1 Nov 19 | 58 | 143 | 99.7 | 26,136 | 1:52.3 |
| Sep 11 | Sep 22 | control | 500 | 1 Nov 24 | 53 | 24,127 | | | |
| Sep 11 | Sep 22 | trtmnt | 500 | 1 Nov 24 | 53 | 0 | 100.0 | 24,127 | 1:48.3 |

From the results shown in the Table III above, it will be noted that the colony control ranges from 96%–100% mortality. Survivors were mostly nymphs and soldiers which engage in little or no grooming. Both of these castes will die without workers to support them. The data indicates that the 100% concentration of sulfluramid is no more effective than the 50% concentration at the 1% treatment release level.

The test units were designed to provide realistic conditions for the compositions to come off by abrasion or dampness. Therefore, the composition was subjected to realistic conditions and the test unit also provides realistic conditions for grooming and trophallaxis to occur within the soil chambers and wood galleries. Provision was also made to permit sick termites to be isolated from healthy termites, as is a normal social habit. The experiments indicate that lethal dosing occurs throughout the population prior to the onset of mortality so that by the time massive mortality sets in, the termites' behavioral mechanisms of isolation and walling off are too late and ineffective.

It will be noted that despite the relatively high concentrations—that is, 50% and 100%—of active ingredient, the grooming continues and the groomers are not repelled by these high dosages. This should be contrasted with the upper limit of 30 parts per million when incorporated in a bait.

The tests demonstrate that a minimum kill ratio in the range of 1 to 42 to 1 to 62 can be expected in the soil environment. Therefore, a 1 to 50 minimum kill ratio could be taken as average. Further studies indicate that the kill ratio maxima exceeds 1 to 1,000. The minima of 1 to 50 therefore appears to very conservative, indicating that it is realistic to trap 2% of the population, treat the trapped population, and subsequently release them. Upon release they will be effective to kill most of the colonies. Colonies of termites typically range from 1 million to 10 million so that trapping of between 20,000 and 200,000 termites, treating them and subsequently releasing them should be effective to eradicate the colony. Trapping of that number of termites is practical within two weeks at most sites.

The efficacy of different concentrations of sulfluramid in ink having the composition above has been investigated. Compositions with concentrations of 50%, 100%, 150% and 200% sulfluramid were made and applied to termites by blotting dorsally onto the termites with the latex cosmetic sponge. One treated termite was then placed in a 14 cm plastic petri dish lined with filter paper to act as food, together with 1,000 untreated termites. Mortality was recorded weekly with the dead termites removed and the old filter paper removed and replaced with new filter paper. The results are shown on Table IV below.

TABLE IV

| | TREATED | | | | UNTREATED |
|---|---|---|---|---|---|
| Treatment # | 1 | 2 | 3 | 4 | 5 |
| % Concent'n | 50 | 100 | 150 | 200 | 0 |
| Total # | 1001 | 1001 | 1001 | 1001 | 1000 |
| 0 | 0.00 | 0.00 | 0.00 | 0.00 | 0.00 |
| 25 | 17.98 | 37.31 | 18.00 | 27.49 | nr |
| 32 | 60.38 | 93.78 | 18.93 | 45.52 | nr |
| 42 | 74.67 | 99.05 | 33.56 | 57.86 | nr |
| 49 | 90.73 | 100.00 | 50.64 | 78.27 | 16.45 |
| 56 | 95.02 | 100.00 | 68.43 | 89.98 | 24.02 |

Days after Treatment
nr = actual number not recorded, general observation taken.

It will be observed that by day 56 of the experiment, 95% mortality was observed with the 50% composition; 100% mortality with the 100% composition; and 68.4% mortality with the 150% composition; and 89.9% mortality with the 200% composition. The untreated control had a mortality rate of 24.1%.

The tests indicate that a concentration of sulfluramid in ink of between 50% and 100% is optimum although concentrations of up to 200% are effective.

Subsequent tests also indicated the extent to which the active ingredient is transmitted through a population. The result of introducing a single treated termite into a group of 500, 1,000, 1,500 and 2,000 untreated termites respectively after treatment with a composition of Example II above. It can be seen from Table V below that a mortality of 67.55%, i.e. a kill ratio of up to 1 to 1,129 has been attained in the group containing 2,000 termites.

TABLE V

| | TREATMENTS | | | |
|---|---|---|---|---|
| Treatment # | 1 | 2 | 3 | 4 |
| # UNTREATED | 500 | 1000 | 1500 | 2000 |
| # TREATED | 1 | 1 | 1 | 1 |
| TOTAL # | 501 | 1001 | 1501 | 2001 |
| 0 | 0.00 | 0.00 | 0.00 | 0.00 |
| 18 | 61.17 | H, nr | H, nr | H, nr |
| 25 | 85.12 | 5.24 | H, nr | H, nr |
| 35 | 100.00 | 45.00 | 31.17 | 15.59 |
| 43 | 100.00 | 57.84 | 63.59 | 53.37 |
| 51 | 100.00 | 84.74 | 72.78 | 67.55 |
| | CONTROLS | | | |
| Treatment # | 5 | 6 | 7 | 8 |
| # UNTREATED | 500 | 1000 | 1500 | 2000 |
| # TREATED | 1 | 1 | 1 | 1 |
| TOTAL # | 501 | 1001 | 1501 | 2001 |
| 0 | 0.00 | 0.00 | 0.00 | 0.00 |
| 18 | H, nr | H, nr | H, nr | H, nr |
| 25 | H, nr | H, nr | H, nr | H, nr |
| 35 | 11.77 | 11.66 | 10.79 | 9.87 |
| 43 | 17.71 | 12.21 | 11.05 | 10.09 |
| 51 | 25.84 | 15.88 | 2.04 | 11.12 |

Days after Treatment
H = termites are healthy
nr = actual numbers not recorded, general observation shown Further testing was utilized to investigate the mechanism by which the active ingredient was transferred. Initially, groups of 100 termites each treated with Example II were introduced into a population of untreated termites at ratios of 1 to 1, 1 to 5, and 1 to 10 for one day. After one day exposure, the untreated termites were transferred to groups of 100 unexposed termites at ratios of 5 to 100 and 2 to 100. Initial transfer of the active ingredient from the treated termites to the untreated termites would occur by grooming. Subsequent transfer of the active ingredient between the untreated termites would then be by way of trophallaxis. The results of this test are indicated below in Table VI, indicating that the social behaviour of both grooming and trophallaxis is utilized to disseminate the active ingredient throughout the insect population.

TABLE VI

Average percent mortality of three replicates of *Reticulitermes flavipes* following exposure to sulfluramid via trophallaxis from carriers who received oral doses at various ratios of exposure to topically treated termites. Topical treatment by dorsal blotter application of 100% sulfluramid in resinous solution.

| Grooming Ratio | Trophallxis Ratio | Grooming X Troph. Ratio | % Mort. (day 34) | % Mort. (day 51) |
|---|---|---|---|---|
| 1:1 | 1:20 | 1:20 | 100 | 100 |
| 1:1 | 1:50 | 1:50 | 91.5 | 100 |
| 1:5 | 1:20 | 1:100 | 95.6 | 100 |
| 1:5 | 1:50 | 1:250 | 27.8 | 97.8 |
| 1:10 | 1:20 | 1:200 | 88.9 | 100 |
| 1:10 | 1:50 | 1:500 | 18.6 | 87.9 |
| 0:10 | 0:50 | 0:500 | 14.0 | 56.0 |

From the above results it will be seen that a composition comprising an active ingredient of sulfluramid and a carrier of an ink as exemplified above may be applied topically to termites and under realistic conditions will be groomed and spread by trophallaxis. Concentrations of active ingredient from that used in baits, namely 0.1% (0.1 gm/1 ml.) up to 200% (2 gm/1 ml.) will be effective, preferably from 50% to 200% but most preferably at concentrations from 50% to 100%.

As noted above, it is necessary for the composition to adhere to the cuticle of the termite, to be water resistant and to be groomable. It is also desirable but not essential that the composition is visible after application to identify treated insects. The ink used in the tests noted above satisfied these criteria. Moreover it was observed that the compositions when applied appeared to promote grooming activity. Surprisingly however, when the same compositions were applied to cardboard to be used as a bait, they were strongly avoided.

Tests conducted on termites indicate other suitable carriers exist in the general class of inks as set out in Table VII below.

TABLE VII

| | | | |
|---|---|---|---|
| 1. Sanford Sharpie, permanent marker | | | |
| a. | Black | good application but groomed or chipped off | X |
| b. | Orange | good application but groomed or chipped off | X |
| c. | Purple | good application but groomed or chipped off | X |
| d. | Yellow | good application but groomed or chipped off | * |
| e. | Green | good application, good visibility, good adhesion | * |
| f. | Red | good application, good visibility, good adhesion | * |
| g. | Blue | good application, good visibility, good adhesion | * |
| 2. Oil 300 | | | |
| a. | Red | good application, good visibility, good adhesion | * |
| 3. Selectum | | | |
| a. | 59–150(Red) | poor application and adhesion | X |
| 4. Nestler Marker | | | |
| | Red | poor application and adhesion | X |
| 5. Berol | | | |
| a. | Prismacolor Art Marker Red | poor application and adhesion | X |
| b. | Liquid Tip Red | poor application and adhesion | X |
| 6. Fabric Painters | | | |
| a. | Red | poor application and adhesion | X |
| 7. Pilot Fluorescent | | | |
| a. | Pink | poor adhesion and poor visibility | X |
| 8. Major Accent | | | |
| a. | Pink | poor adhesion and poor visibility | X |
| 9. Expo Dry Erase Marker (fine) | | | |
| a. | Red | fair application, good visivility, good adhesion | * |
| 10. Staedtler Permanent | | | |
| a. | Blue | fair application, good visivility, good adhesion | * |
| b. | Orange | fair application, groomed or worn off | X |
| c. | Red | fair application, groomed or worn off | X |
| d. | Top Star Fluor Green | poor visibility and poor adhesion | X |
| e. | Non-permanent (fine) Red | poor application and poor adhesion | X |

*Good visibility and not worn off after 10 days
X Poor visibility, or poor application, or poor adhesion after 10 days It will be noted from Table VII that a number of inks exhibited the desirable characteristics for application to termites.

The results set out in Table VII were obtained using ink alone and further tests were conducted to determine the effect of admixture of different toxicants at various concentrations with the ink. The results of these tests are set out in Table VIII below. The tests were conducted utilizing an ink as exemplified above and a commercial composition of barium metaborate monohydrate sold under the trade name Busan 11-M1 (Buckman Laboratories of Canada) which was representative of a fine textured inorganic toxicant. Percentage concentrations of 0%, 5%, 10%, 20%, 40%, 80% and 160% of Busan 11-M1 were made in the ink. A polyurethane foam plug 3.5 cm in diameter was used to blot each of the compositions onto a sheet of aluminum foil and observations were made on coating of the composition. The sheets were permitted to dry thoroughly at room temperature for several days, and then an evaluation was made of the relative ease with which the composition could be chipped to simulate grooming. This evaluation was made under microscopic examination of the surface of the compositions which were scratched with a sharp edge of a pen knife and a pin to simulate the grooming. The relative ease of grooming was recorded. A drop of water was then applied to the center of each drop mark and at value intervals the water droplets were examined microscopically for dissolution of the composition. This was taken as an indication of the water resistance of the composition.

Subsequently the same procedure was used to compare 10%, 50% and 100% concentrations of additional inorganic chemical toxicants, namely borax, boric acid, zinc borate, disodium octaborate tetrahydrate (known as Timbor), sodium hexafluorosilicate, diatomaceous earth. Finally two slow acting organic insecticides, sulfluramid available from Griffin and hydramethylnon available from Cyanamid Canada, were evaluated in the same manner. Preliminary mixtures of sulfluramid at 50%, 100%, 200%, 300%, 400% and 500% concentration (that is 5 grams per 1 ml. of ink) indicated that at 200% and above the composition became an increasingly viscous paste. Hydramethylnon became an unworkably viscous paste above 100% and failed to dissolve completely at 200% concentration (2 grams per 1 ml of ink). Therefore percent concentrations of 140%, 120%, 100%, 90%, 80%, 70%, 60%, 50%, 40%, 30% and 20% were evaluated by blotting for sulfluramid and percent concentrations of 100%, 90%, 80%, 70%, 60%, 50%, 40%, 30%, 20% were evaluated by blotting for hydramethylnon.

TABLE VIII

EFFECT OF CONCENTRATION OF ACTIVES IN INK ON WATERPROOFING AND CAKING

| % Conc. | Sul. | Hyd. | Bus. | Bor. | Tim. | Brx. | ZnB. | Dia. | Hex. |
|---|---|---|---|---|---|---|---|---|---|
| 160 | — | — | 2C | — | — | — | — | — | — |
| 140 | 1 | — | — | — | — | — | — | — | — |
| 120 | 1 | — | — | — | — | — | — | — | — |
| 100 | 1 | 3C | — | 2C | 2C | 1C | 1C | 0C | 0C |
| 90 | 1 | 3C | — | — | — | — | — | — | — |
| 80 | 1 | 2C | 2C | — | — | — | — | — | — |
| 70 | 1 | 1C | — | — | — | — | — | — | — |
| 60 | 0 | 1C | — | — | — | — | — | — | — |
| 50 | 0 | 1C | — | 1 | 1 | 1 | 1C | 0 | 0 |
| 40 | 0 | 0C | 1 | — | — | — | — | — | — |
| 30 | 0 | 0 | — | — | — | — | — | — | — |
| 20 | 0 | 0 | 0 | — | — | — | — | — | — |
| 10 | — | — | 0 | 0 | 0 | 0 | 0 | 0 | 0 |
| 5 | — | — | 0 | — | — | — | — | — | — |

C, caking
0, no detectable dissolution in water drop after 1 hour
1, barely detectable dissolution in water drop
2, moderate dissolution in water drop
3, substantial dissolution in water drop
—, not examined No caking of the Busan 11-M1 composition was observed at 5%, 10%, 20% and 40% concentrations. Slight caking was observed at 80% and serious caking was observed at 160% which resulted in very poor and blotchy application of the composition to the aluminum foil. With the increasing concentration there was a corresponding continuous increase in the ease with which the composition could be chipped and scraped off the aluminum foil. At 0%, 5% and 10% concentration the composition was scraped off with difficultly; at 80% and 160% concentration the composition flaked off too easily. Concentrations of 20% and 40% was scratched off with moderate force and thus 20% and 60% Busan 11-M1 with ink was judged to be the optimal range for chipping by a termite grooming. One hour after application of the water droplet no dissolution of the composition was evident at 20% and below. At 40% and above, slight dissolution was evident after 1 hour. Thus the composition for maximal water resistant for Busan 11-M1 was judged to be between 20% and 40%. As may be seen from Table VIII, an increase in concentrations tended to reduce the water resistance of the composition. Thus compositions in the ranges set out below exhibited the required characteristics of water resistance, ease of application and groomability.

| Applicable, Non-Caking, Water-Resistant Compositions | |
|---|---|
| sulfluramid | >140% |
| hydramethylon | 30%–40% |
| Busan 11-M1 | 40%–80% |
| Boric Acid | 50%–100% |
| Timbor | 50%–100% |
| Borax | 50%–100% |
| Zinc Borate | 10%–50% |
| diatomaceous earth | 50%–100% |
| sodium hex | 50%–100% |

Effective transfer of the composition to the insects is important. This is accomplished most readily by arranging a number of the insects on a flat surface as a single layer and mechanically applying the composition to the dorsal area. The preferred applicator is shown in more fully in FIG. 6 and includes a resilient absorbent material 59 with a rigid backing 60. In the preferred form of applicators, the resilient material 59 is a latex sponge such as that sold as Rialto cosmetic sponge. A number of synthetic foams and alternate pad size have been evaluated to determine their suitability as applicators. The results of the tests are shown in Table IX below.

TABLE IX

SYNTHETIC FOAM AND FIBRE PADS RANKED IN ORDER OF NUMBER OF UNIFORMLY APPLIED BLOTS OF SHARPIE PERMANENT MARKER INK APPLIED TO ALUMINUM FOIL SHEETS

| Rank | Material | # Uniform Blots | Comments | Pore Size |
|---|---|---|---|---|
| 1. | Rialto cosmetic sponge (latex) | 50+ | very uniform | ca. 100 μm |
| 2. | Dr. Scholl's inserts (rubber side) | 37 | very uniform | ca. 50–100 μm |

TABLE IX-continued

SYNTHETIC FOAM AND FIBRE PADS RANKED IN ORDER OF NUMBER
OF UNIFORMLY APPLIED BLOTS OF SHARPIE PERMANENT MARKER
INK APPLIED TO ALUMINUM FOIL SHEETS

| Rank | Material | # Uniform Blots | Comments | Pore Size |
|---|---|---|---|---|
| 3. | Rialto polymethane foam cosmetic disc | 33 | initial blots runny | ca. 250 μm |
| 4. | Latex foam cosmetic pads (cut surface) | 20 | too runny then uneven | ca. 100 μm |
| 5. | Polyurethane envelop sealing sponge | 15 | initial blots too runny | ca. 250 μm |
| 6. | Envelop sealing bottle (Grand & Toy) | 15 | initial blots too runny | ca. 500 μM |
| 7. | Dr. School's inserts (fabric side) | 8 | too absorbent | * |
| 8. | Synthetic bath sponge | 7 | runny then uneven | ca. 0.5–3 mm |
| 9. | Cellulose scrub sponge | 5 | uneven, too hard | ca. 1–3 mm |
| 10. | Polyester fiber scrub pad | 1 | very runny then uneven | * |
| 11. | Dr. Scholl's felt shoe inserts | 0 | uneven absorbency & blotting | * |
| 12. | Polyurethane foam scouring pad | 0 | too coarse, blotchy | ca. 0.5–3 mm |

The results show that in general foam pads provide better blotting than fibre pads and that foam rubber latex pads with finer pores provide better blotting than polyurethane foam pads. The highest ranking blotters were latex foam pads with pore sizes approximately 100 μm in diameter or less. It was noted that the surface of the preferred blotters was a formed surface rather than a cut surface so that between the pores there was a smooth non-porous surface area. It will be noted, for example, that item 4 in Table IX is the same material as item 1 in Table IX, except that the surface of the foam in item 4 is cut rather than formed during the molding process so that the surface texture is entirely porous. As will be noted, this dramatically decreases the efficacy as a blotter.

During testing it was observed that latex foam materials are more easily compressed than polyurethane foams and therefore deliver a more gentle compression when applied to the termites. Gentleness of compression is also affected by thickness of the blotter and it is preferred that the resilient material 59 has a thickness of at least 1 cm. It is preferred that the resilient material has a pore size of less than 250 microns and optimally a pore size of 100 micron or less.

It is anticipated however that where higher viscosity compositions are used, then larger pore sizes of the finer polyurethane foams may be desirable.

From the initial tests on applicability and adherability, it was determined that the most suitable composition was a active ingredient of sulfluramid and a carrier of phenolic resin dissolved in solvents selected from the group comprising n-propanol, diacetone alcohol, n-butanol. It was also noted in initial tests that active ingredients other than sulfluramid resulted in agonistic behaviour, that is, biting and lunging, which in turn resulted in increased mortality following treatment as shown in Table X below.

TABLE X

Table 1. Number of agonistic interactions (bites and biting lunges) during ten 1-minute periods of observation immediately blot treatment with 50% formulation of toxicant in marker pen ink.

Dish # (100 termites per dish)

| Treatment | 1 | 2 | 3 | 4 | 5 | Total | Ave. ± S.D. | $L_w$ | sig. |
|---|---|---|---|---|---|---|---|---|---|
| Zinc Borate | 69 | 67 | 43 | 16 | 66 | 261 | 52.2 ± 22.8 | .68 | a |
| Busan II-M1 | 35 | 51 | 25 | 22 | 36 | 169 | 33.8 ± 11.4 | .11 | b |
| Boric Acid | 42 | 30 | 26 | 29 | 30 | 157 | 31.4 ± 6.1 | .01 | b |
| Tim-Bor | 61 | 33 | 27 | 15 | 19 | 155 | 31.0 ± 18.2 | .45 | b |
| Borax | 13 | 13 | 19 | 19 | 25 | 89 | 17.8 ± 5.0 | .51 | c |
| Sod. Hexafl. | 16 | 14 | 9 | 15 | 4 | 58 | 11.6 ± 5.0 | .63 | d |
| Sulfluramid | 3 | 8 | 6 | 8 | 6 | 31 | 6.2 ± 2.0 | .12 | d |
| Hydrameth. | 9 | 7 | 6 | 1 | 2 | 27 | 5.4 ± 3.4 | .03 | d |
| Diatom. E.[1] | 21 | 2 | 1 | 1 | 0 | 25 | 5.0 ± 9.0 | .13 | d |
| Ink Control | 3 | 2 | 3 | 4 | 5 | 17 | 3.4 ± 1.1 | 1.0 | d |
| Unt. Cont. | 2 | 1 | 0 | 1 | 0 | 4 | 0.8 ± 0.7 | | e |

[1]Diatomaceous earth absorbed the ink causing the first treated dish to have a heavy treatment dose while subsequent dishes received very light doses.

Such agonistic behaviour is extreme with some toxicants such as zinc borate and Busan 11-M1. Such agonism is undesirable because it takes effect prior to release and causes mortality among the treated termites thus reducing the average longevity of the treated termites and thereby reducing the desired transmission of toxicant via grooming.

Generalizing for both organic and inorganic toxicants when used in combination with the exemplified ink above, it is believed that the acceptable concentration of toxicants is in the range of 10% to 140% concentration, most typically 50% to 100%.

The above results were obtained using termites. Similar results have also been obtained with other social insects. In tests conducted with carpenter ants, kill ratios of 1:100 were obtained with a composition of Example I above. Comparable results were not obtained using a 50% concentration of hydramethylnon. It is believed that a 50% concentration of hydramethylnon is too high due to the particular sensitivity of carpenter ants to this particular toxicant. It is anticipated that lower concentrations of methylnon will provide an effective composition. These results are shown in Table XI below.

TABLE XI

Table Comparison of sulfuramid and hydramethyhion in topical resinous formulations at a ratio of 1 treated to 100 untreated carpenter ants, *Camponotus pennsylvanicus.*

| | INK TREATED (CHOICE) number of dead ants -replicants- | | | | % of | HYDRAMETHYLNON + INK number of dead ants -replicates- | | | | % of | SULFURAMID + INK number of dead ants -replicates- | | | | % of |
|---|---|---|---|---|---|---|---|---|---|---|---|---|---|---|---|
| Day | 1 | 2 | 3 | 4 | dead ants* | 1 | 2 | 3 | 4 | dead ants* | 1 | 2 | 3 | 4 | dead ants* |
| 1 | 0 | 0 | 0 | 0 | 0 | 0 | 0 | 0 | 0 | 0 | 0 | 0 | 0 | 0 | 0 |
| 21 | 6 | 10 | 2 | 3 | 5.25 | 0 | 10 | 7 | 10 | 6.75 | 23 | 39 | 13 | 11 | 21.5 |
| 47 | 1 | 0 | 0 | 0 | 5.5 | 5 | 0 | 3 | 0 | 8.75 | 41 | 49 | 58 | 30 | 66 |
| 72 | 5 | 2 | 2 | 3 | 8.5 | 3 | 1 | 1 | 1 | 10.3 | 30 | 10 | 13 | 49 | 91.5 |
| | 80 | 95 | 98 | 100 | | 105 | 81 | 100 | 100 | | 94 | 98 | 84 | 97 | |

*cumulative percentage of mortality

It will be seen, therefore, that the use of an active ingredient with a carrier having the requisite physical properties is effective to utilize the social habits of the insects to disseminate high dosages of the active ingredient through the population to provide control of the population.

The methods and apparatus described above utilise a manual operation for treatment of termites. However, initial treatment as well a subsequent monitoring and control of the population can be conducted on an automatic basis utilizing the apparatus shown in FIG. 7.

Referring therefore to FIG. 7, a trap 70 may be substituted for any of the traps shown in FIG. 1, and includes an external housing 72 with a reservoir 74 located in the base. A floor 76 is located in the housing above reservoir 74 to provide a recruitment chamber 75. Floor 76 has radial grooves 78 leading to a funnel 80. The funnel 80 discharges into a catch tray 82 located above a holding container 84. Catch tray 82 has a hinged floor that releases the contents of the tray into the container 84.

The floor 76 is heated by a heating coil 86 which also conducts heat through the floor and to the inner wall 88 of the housing 72. A spiral wound cardboard roll 90 is located within the inner wall 88 to serve as a feeding substance for termites. The inner wall 88 is also clad with an outer cardboard roll 92 which promotes the passage of termites into the housing 72. An insulated lid 94 is positioned over the housing 72 and has heat conducting inner surfaces of the wall and lid indicated at 96,98 respectively. A heating element 97 is located within the lid 94 to heat the surfaces 96,98.

An aerosol applicator 100 depends from the lid 98 to be positioned over the funnel 80. The aerosol applicator 100 contains a composition of active ingredient and carrier as described above.

Control of the heating elements and the applicator is obtained through electronic components stored in a compartment 102 in the lid 94.

In operation, the heating of the floor and walls provides an optimum environment for termites to live. The cardboard roll 90 provides a source of food and internal passageways. It has been determined that an optimum temperature for termites is between 25° C. and 33° C., with temperatures in excess of 35° C. discouraging termites. Accordingly, in normal operation, the heating element 86 may be controlled to provide a temperature in the preferred range. Termites within the recruitment chamber 75 are free to travel in and out of the chamber and thereby lay pherome trails to recruit other members of the colony.

A portion of the termites from the cardboard roll 90 will migrate along the grooves 78 to the funnel 80 and will fall to be collected in the catch tray 82. Because of the funnel 80, the collected termites in the tray 82 cannot return to recruitment chamber 75. Periodically, the electronic control operates to activate the heating element 97 to elevate the temperature of the walls 96,98. It has been found that temperatures between 33° C. and 44° C., preferably 40° C. can be utilized to drive the termites from the recruitment chamber adn into the catch tray 82. The aerosol is then activated to treat the termites. Thereafter, the hinged floor is released and the treated termites deposited into the container 84. The termites may then be released back into the population, either manually or through release ports 99 in the base.

The provision of the water reservoir 74 and the heating controls permits control of the humidity within the trap and ideally should be between 90% and 100% relative humidity. The enclosed insulated dark humid chamber with the large roll of cardboard 90 is attractive to termites and therefore encourages behavioral recruitment of termites to the trap, resulting in the aggregation of thousands of termites within a matter of days. This facilitates treatment and subsequent release into the population.

An alternative apparatus for treating termites is shown in FIG. 8. In the arrangement of FIG. 8, a funnel 100 is supported by a stand 102. The apex of the funnel is connected to an outlet duct 104 that includes a labyrinth passageway to promote deposition of particulate material passing through the duct. The duct is connected through a filter 106 to a suction pump (not shown).

A screen 108 is supported in the funnel 100 to receive termites that have been separated and cleaned from the traps 12,16. A conical lid 110 fits over the screen 108 and is a close fit on the periphery of the funnel 100. The lid 110 has an inlet 112 connected to a metered aerosol dispenser 114 containing a composition as described above. The metered aerosol 114 may be of any convenient form as described above.

The lid 110 includes vents to permit air to flow from the lid through the screen and out of the outlet duct 104.

In operation, therefore, the termites are deposited on the screen 108, and the lid 110 fitted to the funnel 100. The duct 104 is connected to the source of suction so that an air flow is induced through the screen. The aerosol 114 is operated to dispense a metered dosage of the composition which is drawn by the air flow onto the termites. Any surplus composition passes through the screen and is deposited on the baffle and collected in the filter 106 in the outlet duct 104. Thereafter, the treated termites may be released to return to the colony.

The apparatus of FIG. 8 provides a reusable treatment apparatus which avoids the operator being in direct contact with the composition and controls the discharge of the composition into the atmosphere. Disassembly of the apparatus can be accomplished without direct handling of contaminated surfaces and therefore provides a safer environment for the operator.

I claim:

1. A composition for treating a population of social insects comprising an active ingredient, a solvent and a carrier adherable to the insect to provide a groomable, adherent coating on a selected area of the insect, said active ingredient being a fluoroaliphatic sulfonamide, said carrier being a phenol-formaldehyde novolac resin having a CAS# of 28453-20-5 or 54579-44-1 and said solvent being selected from the group consisting of ethanol, n-propanol, n-butanol and diacetone alcohol, said composition having a concentration of active ingredient, when expressed in grams of active ingredient in milliliters of carrier and solvent, being in the range of 0.001 g/ml to 2 g/ml.

2. A composition according to claim 1 further comprising an attractant for said insect to promote grooming thereof.

3. A composition according to claim 1 wherein the said concentration of active ingredient is within 0.1 g/ml to 1.40 g/ml.

4. A composition according to claim 1 wherein the said concentration of active ingredient is within 0.25 g/ml to 1.00 g/ml.

5. A composition according to claims 1, 3 or 4 wherein the carrier is CK2103.

* * * * *